(12) United States Patent
Dollinger et al.

(10) Patent No.: US 6,297,192 B1
(45) Date of Patent: Oct. 2, 2001

(54) SELECTIVE HERBICIDES BASED ON N-ARYL-TRIAZOLINE(THI)ONS AND N-ARLYSULFONYLAMINO(THIO)CARBONYL-TRIAZOLINE(THI)ONS

(75) Inventors: Markus Dollinger, Overland Park, KS (US); Mark Wilhelm Drewes, Langenfeld (DE); Wilhelm Haas, Pulheim (DE); Klaus-Helmut Müller, Düsseldorf (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/600,576

(22) PCT Filed: Jan. 12, 1999

(86) PCT No.: PCT/EP99/00130

§ 371 Date: Aug. 9, 2000

§ 102(e) Date: Aug. 9, 2000

(87) PCT Pub. No.: WO99/37153

PCT Pub. Date: Jul. 29, 1999

(30) Foreign Application Priority Data

Jan. 24, 1998 (DE) .............................. 198 02 697

(51) Int. Cl.⁷ ................................................ A01N 43/653
(52) U.S. Cl. ............................................................ 504/139
(58) Field of Search ............................................. 504/139

(56) References Cited

U.S. PATENT DOCUMENTS

| 4,318,731 | 3/1982 | Kajioka et al. | 71/92 |
|---|---|---|---|
| 4,702,763 | 10/1987 | Maravetz | 71/90 |
| 4,734,280 | 3/1988 | Braquet | 424/195.1 |
| 4,806,145 | 2/1989 | Maravetz | 71/92 |
| 4,818,275 | 4/1989 | Theodoridis | 71/92 |
| 4,818,276 | 4/1989 | Maravetz et al. | 71/92 |
| 4,845,232 | 7/1989 | Matsui et al. | 548/265 |
| 4,906,284 | 3/1990 | Theodoridis | 71/92 |
| 4,909,831 | 3/1990 | Keifer et al | 71/92 |
| 4,909,833 | 3/1990 | Kajioka et al. | 71/92 |
| 5,006,148 | 4/1991 | Fischer et al. | 71/72 |
| 5,035,740 | 7/1991 | Poss | 71/93 |
| 5,041,155 | 8/1991 | Theodoridis | 71/92 |
| 5,300,480 | 4/1994 | Haas et al. | 504/273 |
| 5,464,810 | 11/1995 | Haas et al. | 504/273 |
| 5,476,946 * | 12/1995 | Linker et al. | 504/273 |
| 5,488,028 | 1/1996 | Haas et al. | 504/193 |
| 5,534,486 | 7/1996 | Müller et al. | 504/273 |
| 5,541,337 | 7/1996 | Müller et al. | 548/263.6 |
| 5,554,761 | 9/1996 | Haas et al. | 548/263.6 |
| 5,597,939 | 1/1997 | Müller et al. | 558/8 |
| 5,631,380 | 5/1997 | Haas et al. | 548/263.4 |
| 5,652,372 | 7/1997 | Müller et al. | 548/263.4 |
| 5,869,681 | 2/1999 | Müller et al. | 548/263.6 |
| 5,994,273 | 11/1999 | Müller et al. | 504/273 |
| 6,077,813 | 6/2000 | Linker et al. | 504/272 |

FOREIGN PATENT DOCUMENTS

| 597360 | 11/1993 | (EP) . |
|---|---|---|
| 341489 | 8/1995 | (EP) . |
| 425948 | 12/1995 | (EP) . |
| 422469 | 5/1996 | (EP) . |
| 431291 | 7/1998 | (EP) . |
| 85/01637 * | 4/1985 | (WO) . |
| 85/04307 | 10/1985 | (WO) . |
| 86/02642 | 5/1986 | (WO) . |
| 86/04481 | 8/1986 | (WO) . |
| 87/03782 | 7/1987 | (WO) . |
| 88/09617 | 12/1988 | (WO) . |
| 90/02120 | 3/1990 | (WO) . |
| 96/11188 | 4/1996 | (WO) . |
| 96/27590 | 9/1996 | (WO) . |
| 97/03056 | 1/1997 | (WO) . |
| 98/12923 * | 4/1998 | (WO) . |

* cited by examiner

Primary Examiner—S. Mark Clardy
(74) Attorney, Agent, or Firm—Joseph C. Gil; Jackie Ann Zurcher

(57) ABSTRACT

The invention relates to novel herbicidal synergistic active compound combinations comprising on the one hand known N-aryl-triazoline(thi)ones and on the other hand known N-arylsulphonylamino(thio)carbonyl-triazoline(thi)ones which can be used particularly successfully for the selective control of weeds in various crops of useful plants.

17 Claims, No Drawings

SELECTIVE HERBICIDES BASED ON N-ARYL-TRIAZOLINE(THI)ONS AND N-ARLYSULFONYLAMINO(THIO)CARBONYL-TRIAZOLINE(THI)ONS

TECHNICAL FIELD OF THE INVENTION

The invention relates to novel herbicidal synergistic active compound combinations comprising on the one hand known N-aryl-triazolin(ethi)ones and on the other hand known N-arylsulphonylamino(thiocarbonyl-triazolin(ethi) ones which can be used particularly successfully for the selective control of weeds in various crops of useful plants.

BACKGROUND OF THE INVENTION

N-Aryl-triazolin(ethi)ones, as herbicidally active substances, form part of the subject-matter of a number of patent applications (cf. DE-A-3024316, DE-A-3514057, DE-A-3636318, EP-A-220952, EP-A-370332, EP-A-597360, EP-A-609734, U.S. Pat. No. 4,702,763, U.S. Pat. No. 4,806,145, U.S. Pat. No. 4,818,275, U.S. Pat. No. 4,906,284, U.S. Pat. No. 4,909,831, U.S. Pat. No. 5,035,740, U.S. Pat. No. 5,041,155, WO-A-8501637, WO-A-8504307, WO-A-8602642, WO-A-8604481, WO-A-8700730, WO-A-8703782, WO-A-8809617, WO-A-9002120, WO-A-9530661).

N-Arylsulphonylamino(thio)carbonyl-triazolin(ethi)ones, as herbicidally active substances, likewise form part of the subject-matter of a number of patent applications (cf. EP-A-341489, EP-A-422469, EP-A425948, EP-A-431291, EP-A-507171, EP-A-534266, WO-A-9611188, WO-A-9627590, WO-A-9627591, WO-A-9703056).

DETAILED DESCRIPTION OF THE INVENTION

Surprisingly, it has now been found that a number of known active compounds from the group of the N-aryl-triazolin(ethi)ones, when used jointly with known herbicidally active compounds from the group of the N-arylsulphonylamino(thio)carbonyltriazolin(ethi)ones, exhibit synergistic effects with respect to their action against broadleaf weeds and can be used particularly advantageously as broad-spectrum combination preparations for the selective control of weeds in crops of useful plants such as, for example, in wheat.

The invention provides selective herbicidal compositions, characterized in that they contain an effective amount of an active compound combination comprising (a) at least one N-aryl-triazolin(ethi)one of the general formula (I)

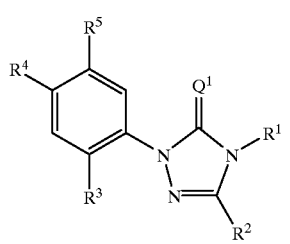

(I)

in which
Q$^1$ represents oxygen or sulphur,
R$_1$ represents optionally halogen-substituted alkyl having 1 to 5 carbon atoms,
R$^2$ represents optionally halogen-substituted alkyl having 1 to 5 carbon atoms,
R$^3$ represents hydrogen or halogen,
R$^4$ represents cyano, thiocarbamoyl or halogen, and
R$^5$ represents nitro, cyano, carboxyl, carbamoyl, thiocarbamoyl, hydroxyl, mercapto, amino, hydroxyamino, aminosulphonyl, halogen, represents in each case optionally cyano-, hydroxyl-, $C_1$–$C_4$-alkoxy-, $C_1$–$C_4$-alkyl-carbonyl- and/or $C_1$–$C_4$-alkoxy-carbonyl-substituted alkyl, alkoxy, alkylthio, alkylsul-phinyl, alkylsulphonyl, alkylcarbonyl, alkoxycarbonyl or alkylamino having in each case 1 to 6 carbon atoms, represents in each case optionally cyano-, carboxyl-, halogen- and/or $C_1$–$C_4$-alkoxy-carbonyl-substituted alkenyl, alkinyl, alkenyloxy or alkinyloxy having in each case 2 to 6 carbon atoms, represents in each case optionally halogen-substituted alkylcarbonylamino, alkoxycarbonylamino, alkylsulphonylamino, N,N-bis-alkylsulphonyl-amino or N-alkylcarbonyl-N-alkylsulphonyl-amino having in each case 1 to 6 carbon atoms in the alkyl groups, or represents in each case optionally cyano-, halo-gen-, $C_1$–$C_4$-alkyl-, $C_1$–$C_4$-halogenoalkyl-, $C_1$–$C_4$-alkoxy- or $C_1$–$C_4$-halo-genoalkoxy-substituted N-phenylcarbonyl-N-alkylsulphonyl-amino, N-pyridylcarbonyl-N-alkylsulphonyl-amino, N-furylcarbonyl-N-alkylsulphonyl-amino or N-thienylcarbonyl-N-alkylsulphonyl-amino having in each case 1 to 6 carbon atoms in the alkyl groups,
("active compounds of group 1") and (b) at least one N-arylsulphonylamino(thio)carbonyl-triazolin(ethi)one of the general formula (II)

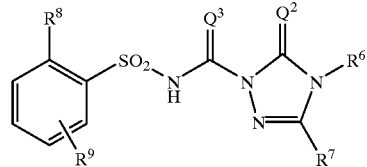

(II)

in which
Q$^2$ and Q$^3$ each represent oxygen or sulphur,
R$^6$ represents in each case optionally cyano-, halogen- or $C_1$–C4-alkoxy-substituted alkyl, alkenyl, alkinyl, alkoxy, alkenyloxy, alkylamino or dialkylamino having in each case up to 6 carbon atoms, or represents in each case optionally cyano-, halogen- or $C_1$–$C_4$-alkyl-substituted cycloalkyl, cycloalkylalkyl or cycloalkylamino having in each case 3 to 6 carbon atoms in the cycloalkyl groups and optionally 1 to 4 carbon atoms in the alkyl moiety,
R$^7$ represents hydrogen, represents halogen, represents in each case optionally cyano-, halogen- or $C_1$–$C_4$-alkoxy-substituted alkyl, alkoxy, alkylthio, alkylamino, dialkylamino, alkenyl, alkinyl, alkenyloxy, alkinyloxy, alkenylthio, alkinylthio, alkenylamino or alkinylamino having in each case up to 6 carbon atoms, or represents in each case optionally cyano-, halogen- or $C_1$–$C_4$-alkyl-substituted cycloalkyl, cycloalkyloxy, cycloalkylthio, cycloalkylamino or cycloalkylalkyl having in each case 3 to 6 carbon atoms in the cycloalkyl groups and optionally 1 to 4 carbon atoms in the alkyl moiety,
R$^8$ represents nitro, cyano, halogen, phenyl, phenoxy, represents in each case optionally cyano-, halogenor $C_1$–$C_4$-alkoxy-substituted alkyl, alkylcarbonyl, alkoxy, alkoxycarbonyl, alkylthio, alkylsulphinyl, alkylsulphonyl, dialkylaminosulphonyl, alkylamino, alkenyl, alkenyloxy, alkenylthio, alkenylamino, alkinyl, alkinyloxy, alkinylthio having in each case up to 6 carbon atoms, or represents in each case optionally cyano-, halogen- or $C_1$–$C_4$-alkyl-substituted cycloalkyl, cycloalkyloxy, cycloalkylthio, cycloalkylamino having in each case 3 to 6 carbon atoms in the cycloalkyl groups, and $R^9$ represents hydrogen, nitro, cyano, halogen, phenyl, phenoxy, represents in each case optionally cyano-, halogen- or $C_1$–$C_4$-alkoxy-substituted alkyl, alkylcarbonyl, alkoxy, alkoxycarbonyl, alkylthio, alkylsulphinyl, alkylsulphonyl, alkylamino, alkenyl, alkenyloxy, alkenylthio, alkenylamino, alkinyl, alkinyloxy or alkinylthio having in each case up to 6 carbon atoms, or represents in each case optionally cyano-, halogen- or $C_1$–$C_4$-alkyl-substituted cycloalkyl, cycloalkyloxy, cycloalkylthio, cycloalkylamino having in each case 3 to 6 carbon atoms in the cycloalkyl groups, and/or a salt of a compound of the formula (II)

("active compounds of group 2")

where generally 0.01 to 100 parts by weight of an active compound of group 2—i.e. of the general formula (II)—are present per part by weight of an active compound of group 1—i.e. of the general formula (I).

Of particular interest are selective herbicidal compositions according to the invention which are characterized in that they contain an active compound combination comprising (a) at least one N-aryl-triazolin(ethi)one of the general formula (I), in which $Q^1$ represents oxygen or sulphur, $R^1$ represents in each case optionally fluorine- and/or chlorine-substituted methyl, ethyl, n- or i-propyl, n-, i-, s- or t-butyl, $R^2$ represents in each case optionally fluorine- and/or chlorine-substituted methyl, ethyl, n- or i-propyl, n-, i-, s- or t-butyl, $R^3$ represents hydrogen, fluorine, chlorine or bromine, $R^4$ represents cyano, thiocarbamoyl, fluorine, chlorine or bromine, and $R^5$ represents nitro, cyano, carboxyl, carbamoyl, thiocarbamoyl, hydroxyl, mercapto, amino, hydroxyamino, aminosulphonyl, fluorine, chlorine, bromine, represents in each case optionally cyano-, hydroxyl-, methoxy-, ethoxy-, acetyl-, propionyl-, methoxycarbonyl- and/or ethoxy-carbonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, acetyl, propionyl, n- or i-butyroyl, methoxycarbonyl, ethoxycarbonyl, n- or i-propoxycarbonyl, methylamino, ethylamino, n- or i-propylamino, n-, i-, s- or t-butylamino, represents in each case optionally cyano-, carboxyl-, fluorine-, chlorine-, bromine-, methoxycarbonyl- and/or ethoxy-carbonyl-substituted ethenyl, propenyl, butenyl, ethinyl, propinyl, butinyl, propenyloxy, butenyloxy, propinyloxy or butinyloxy, represents in each case optionally fluorine- and/or chlorine-substituted acetylamino, propionylamino, methoxycarbonylamino, ethoxycarbonylamino, methylsulphonylamino, ethylsulphonylamino, n- or i-propylsulphonylamino, n-, i-, s- or t-butylsulphonyl-amino, N,N-bis-methylsulphonyl-amino, N,N-bis-ethylsulphonyl-amino, N-ethylsulphonyl-N-methylsulphonyl-amino, N-acetyl-N-methylsulphonyl-amino, N-propionyl-N-methylsulphonyl-amino, N-n-butyroyl-N-methyl-sulphonyl-amino, N-i-butyroyl-N-methylsulphonyl-amino, N-acetyl-N-ethyl-sulphonyl-amino, N-propionyl-N-ethylsulphonyl-amino, N-n-butyroyl-N-eth-ylsulphonyl-amino, N-i-butyroyl-N-ethylsulphonyl-amino, or represents in each case optionally cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted N-phenylcarbonyl-N-methylsulphonyl-amino, N-phenylcarbonyl-N-ethylsulphonyl-amino, N-thienylcarbonyl-N-methylsulphonyl-amino or N-thienylcarbonyl-N-ethylsulphonyl-amino, ("active compounds of group 1") and (b) at least one N-arylsulphonylamino(thio) carbonyltriazolin(ethi)one of the general formula (II) in which $Q^2$ and $Q^3$ each represent oxygen or sulphur, $R^6$ represents in each case optionally cyano-, fluorine-, chlorine-, methoxy- or ethoxy-substituted methyl, ethyl, n- or i-propyl, n-, i-, s- or t-butyl, ethenyl, propenyl, butenyl, ethinyl, propinyl, butinyl, methoxy, ethoxy, n- or i-propoxy, n-, i-, s- or t-butoxy, propenyloxy, butenyloxy, methylamino, ethylamino, n- or i-propylamino, n-, i-, s- or t-butylamino, dimethylamino or diethylamino, or represents in each case optionally cyano-, fluorine-, chlorine-, bromine-, methyl-, ethyl-, n- or i-propyl-substituted cyclopropyl, cyclobutyl, cyclopentyl, cyclohexyl, cyclopropylmethyl, cyclobutylmethyl, cyclopentylmethyl, cyclohexylmethyl, cyclopropylamino, cyclobutylamino, cyclopenty-lamino or cyclohexylamino, $R^7$ represents fluorine, chlorine, bromine, represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino, diethylamino, ethenyl, propenyl, butenyl, ethinyl, propinyl, butinyl, ethenyloxy, propenyloxy, butenyloxy, propinyloxy, butinyloxy, ethenylthio, propenylthio, butenylthio, propinylthio, butinylthio butinyloxy, ethenylthio, propenylthio, butenylthio, propinylthio, butinylthio, propenylamino, butenylamino, propinylamino or butinylamino, or represents in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl or cyclohexylmethyl, $R^8$ represents nitro, cyano, fluorine, chlorine, bromine, represents in each case optionally cyano-, fluorine-, chlorine-, methoxy- or ethoxy-substituted methyl, ethyl, n- or i-propyl, n-, i-, s- or t-butyl, acetyl, propionyl, n- or i-butyroyl, methoxy, ethoxy, n- or i-propoxy, n-, i-, s- or t-butoxy, methoxycarbonyl, ethoxycarbonyl, n- or i-propoxycarbonyl, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, ethenyl, propenyl, butenyl, propenyloxy, butenyloxy, propenylthio, butenylthio, propenylamino, butenylamino, ethinyl, propinyl, butinyl, propinyloxy, butinyloxy, propinylthio or butinylthio, or represents in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino, $R^9$ represents hydrogen, nitro, cyano, fluorine, chlorine, bromine, represents in each case optionally cyano-, fluorine-, chlorine-, methoxy- or ethoxy-substituted methyl, ethyl, n- or i-propyl, n-, i-, s- or t-butyl, acetyl, propionyl, n- or i-butyroyl, methoxy, ethoxy, n- or i-propoxy, n-, i-, s- or t-butoxy, methoxycarbonyl, ethoxycarbonyl, n- or i-propoxycarbonyl, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, ethenyl, propenyl, butenyl, propenyloxy, butenyloxy, propenylthio, butenylthio, propenylamino, butenylamino, ethinyl, propinyl, butinyl, propinyloxy, butinyloxy, propinylthio or butinylthio, or represents in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino, and/or a salt of a compound of the formula (II)

("active compounds of group 2")

where in general 0.05 to 50 parts by weight of an active compound of group 2—i.e. of the formula (II)—are present per part by weight of an active compound of group 1—i.e. of the formula (I).

Of very particular interest are selective herbicidal compositions according to the invention which are characterized in that they contain an active compound combination comprising (a) at least one N-aryl-triazolin(ethi)one of the general formula (I), in which
$Q_1$ represents oxygen or sulphur,
$R_1$ represents methyl, ethyl or difluoromethyl,
$R^2$ represents methyl, ethyl, difluoromethyl, trifluoromethyl, fluoroethyl, difluoroethyl, trifluoroethyl, tetrafluoroethyl or pentafluoroethyl,
$R^3$ represents fluorine or chlorine,
$R^4$ represents cyano, thiocarbamoyl, chlorine or bromine, and $R^5$ represents nitro, cyano, carboxyl, carbamoyl, thiocarbamoyl, hydroxyl, mercapto, amino, fluorine, chlorine, bromine, represents in each case optionally cyano-, methoxy-, ethoxy-, methoxycarbonyl- and/or ethoxy-carbonyl-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, methoxycarbonyl, ethoxycarbonyl, n- or i-propoxycarbonyl, methylamino, ethylamino, n- or i-propylamino, represents in each case optionally cyano-, carboxyl-, fluorine-, chlorine-, bromine-, methoxycarbonyl- and/or ethoxycarbonyl-substituted ethenyl or propenyl, represents propenyloxy, butenyloxy, propinyloxy or butinyloxy, represents in each case optionally fluorine- and/or chlorine-substituted methylsulphonylamino, ethylsulphonylamino, n- or i-propylsulphonylamino, n-, i-, s- or t-butylsulphonylamino, N,N-bis-methylsulphonyl-amino, N,N-bis-ethylsulphonyl-amino, N-ethylsulphonyl-N-methylsulphonyl-amino, N-acetyl-N-methylsulphonyl-amino, N-propionyl-N-methylsulphonyl-amino, N-n-butyroyl-N-methylsulphonyl-amino, N-i-butyroyl-N-methylsulphonyl-amino, N-acetyl-N-ethylsulphonyl-amino, N-propionyl-N-ethylsulphonyl-amino, N-n-butyroyl-N-ethylsulphonyl-amino, N-i-butyroyl-N-ethylsulphonyl-amino, or represents in each case optionally cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted N-phenylcarbonyl-N-methylsulphonyl-amino, N-phenylcarbonyl-N-ethylsulphonyl-amino, N-thienylcarbonyl-N-methylsulphonyl-amino or N-thienylcarbonyl-N-ethylsulphonyl-amino, ("active compounds of group 1") and (b) at least one N-arylsulphonylamino(thio) carbonyltriazolin(ethi)one of the general formula (II) in which
$Q^2$ and $Q^3$ each represent oxygen or sulphur,
$R^6$ represents in each case optionally fluorine-, chlorine-, methoxy- or ethoxy-substituted methyl, ethyl, methoxy or ethoxy, or represents cyclopropyl,
$R^7$ represents chlorine, bromine, represents in each case optionally fluorine-, chlorine-, methoxy- or ethoxy-substituted methyl, ethyl, n- or i-propyl, methoxy, ethoxy, n- or i-propoxy, methylthio, ethylthio, n- or i-propylthio, methylamino, ethylamino, n- or i-propylamino, represents dimethylamino, propenylthio, propinylthio or represents cyclopropyl,
$R^8$ represents fluorine, chlorine, bromine, represents in each case optionally fluorine-, chlorine-, methoxy- or ethoxy-substituted methyl, ethyl, n- or i-propyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, or represents cyclopropyl,
$R^9$ represents hydrogen, nitro, cyano, fluorine, chlorine, bromine, represents in each case optionally fluorine-, chlorine-, methoxy- or ethoxy-substituted methyl, ethyl, n- or i-propyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, n- or i-propylsulphinyl, methylsulphonyl, ethylsulphonyl, n- or i-propylsulphonyl, or represents cyclopropyl, and/or a salt of a compound of the formula (II) ("active compounds of group 2") where generally 0.1 to 10 parts by weight of an active compound of group 2—i.e. of the formula (II)—are present per part by weight of an active compound of group 1—i.e. of the formula (I).

Instead of the pure active compounds of the formula (II), it is also possible to use salts of the compounds of the formula (II) with metals and/or with basic nitrogen compounds in the active compound combinations according to the invention.

Preference is given here to salts of the compounds of the formula (II) with alkali metals, such as, for example, lithium, sodium, potassium, rubidium or caesium, particularly preferably with sodium or potassium, with alkaline earth metals, such as, for example, magnesium, calcium or barium, particularly preferably with calcium, or with earth metals, such as, for example, aluminium.

Preference is furthermore given to salts of the compounds of the formula (II) with ammonia, with $C_1$–$C_6$-alkyl-amines such as, for example, with methylamine, ethylamine, n- or i-propylamine, n-, i-, s- or t-butylamine, n-, i-, s- or t-pentylamine, with di-($C_1$–$C_6$-alkyl)-amines such as, for example, dimethylamine, diethylamine, dipropylamine, diisopropylamine, dibutylamine, diisobutylamine, di-s-butylamine, dipentylamine, diisopentylamine, di-s-pentylamine and dihexylamine, with tri-($C_1$–$C_4$-alkyl)-amines, such as, for example, trimethylamine, triethylamine, tripropylamine, tributylamine and N-ethyl-diisopropylamine, with $C_3$–$C_6$-cycloalkylamines, such as, for example, cyclopentylamine or cyclohexylamine, with di-($C_3$–$C_6$-cycloalkyl)-amines, such as, for example, dicyclopentylamine or dicyclohexylamine, with N-$C_1$–$C_4$-alkyl-$C_3$–$C_6$-cycloalkylamines, such as, for example, N-methyl-cyclopentylamine, N-ethyl-cyclopentylamine, N-methyl-cyclohexylamine or N-ethyl-cyclohexylamine, with N,N-di-($C_1$–$C_4$-alkyl)-$C_3$–$C_6$-cycloalkyl-amines, such as, for example, N,N-dimethyl-cyclopentylamine, N,N-diethyl-cyclopentylamine, N,N-dimethyl-cyclohexylamine or N,N-diethyl-cyclohexylamine, with N-$C_1$–$C_4$-alkyl-di-($C_3$–$C_6$-cycloalkyl)-amines, such as, for example, N-methyl-dicyclopentylamine, N-ethyl-dicyclopentylamine, N-methyl-dicyclohexylamine or N-ethyl-dicyclohexylamine, with phenyl-$C_1$–$C_4$-alkyl-amines, such as, for example, benzylamine, 1-phenyl-ethylamine or 2-phenyl-ethylamine, with N-$C_1$–$C_4$-alkylphenyl-$C_1$–$C_4$-alkyl-amines, such as, for example, N-methyl-benzylamine or N-ethylbenzylamine, or with N,N-di-($C_1$–$C_4$-alkyl)-phenyl-$C_1$–$C_4$-alkyl-amines, such as, for example, N,N-dimethyl-benzylamine or N,N-diethyl-benzylamine, or with optionally fused and/or $C_1$–$C_4$-alkyl-substituted amines, such as, for example, pyridine, quinoline, 2-methyl-pyridine, 3-methyl-pyridine, 4-methyl-pyridine, 2,4-dimethyl-pyridine, 2,5-dimethyl-pyridine, 2,6-dimethyl-pyridine or 5-ethyl-2-methyl-pyridine.

Basic compounds which can be employed for preparing the salts of the compounds of the formula (II) utilizable according to the invention which may be mentioned are: alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n, i-, s- or t-butoxide.

Examples of the compounds of the formula (I) to be used as mixing partners according to the invention which may be mentioned are:

2-(4-cyano-2-fluoro-5-methylsulphonylamino-phenyl)-4-methyl-5-trifluoromethyl-2,4-dihydro-3H-1,2,4-triazol-3-one, 2-(4-cyano-2-fluoro-5-ethylsulphonylamino-phenyl)-4-methyl-5-trifluoromethyl-2,4-dihydro-3H-1,2,4-triazol-3-one, 2-(4-cyano-2-fluoro-5-methylsulphonylamino-phenyl)-4-methyl-5-difluoromethyl-2,4-dihydro-3H-1,2,4-triazol-3-one, 2-(4-cyano-2-fluoro-5-ethylsulphonylamino-phenyl)-4-methyl-5-difluoromethyl-2,4-dihydro-3H-1,2,4-triazol-3-one, 2-(4-cyano-2-fluoro-5-methylsulphonylamino-phenyl)-4-ethyl-5-trifluoromethyl-2,4-dihydro-3H-1,2,4-triazol-3-one, 2-(4-cyano-2-fluoro-5-ethylsulphonylamino-phenyl)-4-ethyl-5-methyl-2,4-dihydro-3H-1,2,4-triazol-3-one, 2-(4-cyano-2-fluoro-5-methylsulphonylamino-phenyl)-4-ethyl-5-difluoromethyl-2,4-dihydro-3H-1,2,4-triazol-3-one, 2-(4-cyano-2-fluoro-5-ethylsulphonylamino-phenyl)-4-ethyl-5-difluoromethyl-2,4-dihydro-3H-1,2,4-triazol-3-one, 2-(4-thiocarbamoyl-2-fluoro-5-methylsulphonylamino-phenyl)-4-methyl-5-trifluoromethyl-2,4-dihydro-3H-1,2,4-triazol-3-one, 2-(4-thiocarbamoyl-2-fluoro-5-ethylsulphonylamino-phenyl)-4methyl-5-trifluoromethyl-2,4-dihydro-3H-1,2,4-triazol-3-one, 2-(4-thiocarbamoyl-2-fluoro-5-methylsulphonylamino-phenyl)-4-methyl-5-difluoromethyl-2,4-dihydro-3H-1,2,4-triazol-3-one, 2-(4-thiocarbamoyl-2-fluoro-5-ethylsulphonylamino-phenyl)-4-methyl-5-difluoromethyl-2,4-dihydro-3H- 1,2,4-triazol-3-one, 2-(4-thiocarbamoyl-2-fluoro-5-methylsulphonylamino-phenyl)-4-ethyl-5-trifluoromethyl-2,4-dihydro-3H-1,2,4-triazol-3-one, 2-(4-thiocarbamoyl-2-fluoro-5-ethylsulphonylamino-phenyl)-4-ethyl-5-trifluoromethyl-2,4-dihydro-3H-1,2,4-triazol-3-one, 2-(4-thiocarbamoyl-2-fluoro-5-methylsulphonylamino-phenyl)4-ethyl-5-difluoromethyl-2,4-dihydro-3H-1,2,4-triazol-3-one, 2-(4-thiocarbamoyl-2-fluoro-5-ethylsulphonylamino-phenyl-4-ethyl-5-difluoromethyl-2,4-dihydro-3H-1,2,4-triazol-3-one.

The compound 2-(4-thiocarbamoyl-2-fluoro-5-ethylsulphonylamino-phenyl)-4-methyl-5-trifluoromethyl-2,4-dihydro-3H-1,2,4-triazol-3-one (I-1)—according to Chem. Abstracts also to be referred to as 4-[4,5-dihydro-4-methyl-5-oxo-(3-trifluoromethyl)-1H-1,2,4-triazol-1-y1]-2-[(ethylsulphonyl)amino]-5-fluoro-benzenecarbothioamide (CAS Reg. No.: 173980-17-1)—may be particularly emphasized as mixing component of the formula (I).

The compounds 2-(4-cyano-2-fluoro-5-ethylsulphonylamino-phenyl)-4-methyl-5-trifluoromethyl-2,4-dihydro-3H-1,2,4triazol-3-one (I-2)—according to Chem. Abstracts also to be referred to as N-[2-cyano-5-[4, 5-dihydro-4-methyl-5-oxo-3-trifluoromethyl-1H-1, 2,4-triazol-1-yl]-4-fluoro-phenyl]-ethanesulphonamide (CAS Reg. No.: 157739-55-4)—and 2-(4-cyano-2-fluoro-5-ethylsulphonylamino-phenyl)-4-ethyl-5-trifluoromethyl-2, 4-dihydro-3H-1,2,4-triazol-3-one (I-3)—according to Chem. Abstracts also to be referred to as N-[2-cyano-5-[4-ethyl-4,5-dihydro-5-oxo-3-trifluoromethyl-1H-1,2,4-triazol-1-yl]-4-fluoro-phenyl]-ethanesulphonamide (CAS Reg. No.: 157739-37-2)—and 2-(4-cyano-2-fluoro-5-methylsulphonylamino-phenyl)-4-methyl-5- difluoromethyl-2,4-dihydro-3H-1,2,4-triazol-3-one (I-4)—according to Chem. Abstracts also to be referred to as N-[2-cyano-5-[3-difluoromethyl-4,5-dihydro-4-methyl-5-thioxo-1H-1,2,4-triazol-1-yl]-4-fluoro-phenyl]-methanesulphonamide (CAS Reg. No.: 157739-46-3)—may furthermore be particularly emphasized as possible mixing components of the formula (I).

The compounds of the formula (I) are described in the patent applications or patents mentioned above for the N-aryl-triazolin(ethi)ones.

Mixing components from the active compounds of group 2 which may be particularly emphasized are:
2-(2-chloro-phenylsulphonylaminocarbonyl)-, 2-(2-bromo-phenylsulphonylaminocarbonyl)-, 2-(2-methyl-phenylsulphonylaminocarbonyl)-, 2-(2-ethyl-phenylsulphonylaminocarbonyl)-, 2-(2-n-propyl-phenylsulphonylaminocarbonyl), 2-(2-i-propyl-phenylsulphonylaminocarbonyl), 2-(2-trifluoromethyl-phenylsulphonylaminocarbonyl)-, 2-(2-methoxy-phenylsulphonylaminocarbonyl)-, 2-(2-ethoxy-phenylsulphonylaminocarbonyl)-, 2-(2-n-propoxy-phenylsulphonylaminocarbonyl)-, 2-(2-i-propoxy-phenylsulphonylaminocarbonyl)-, 2-(2-difluoromethoxy-phenylsulphonylaminocarbonyl)-, 2-(2-trifluoromethoxy-phenylsulphonylaminocarbonyl)-, 2-(2-methoxycarbonyl-phenylsulphonylaminocarbonyl)-, 2-(2-ethoxycarbonyl-phenylsulphonylaminocarbonyl)-, 2-(2-n-propoxycarbonyl-phenylsulphonylaminocarbonyl)-, 2-(2-i-propoxycarbonyl-phenylsulphonylaminocarbonyl)- and 2-(2-chloro-6-methyl-phenylsulphonylaminocarbonyl)-4-methyl-5-methoxy-2,4-dihydro-3H-1,2,4-triazol-3-one, -4-methyl-5-ethoxy-2,4-dihydro-3H-1,2,4-triazol-3-one, -4-methyl-5-n-propoxy-2,4-dihydro-3H-1,2,4-triazol-3-one, -4-methyl-5-i-propoxy-2,4-dihydro-3H-1,2, 4-triazol-3-one, -4-methyl-5-trifluoroethoxy-2,4dihydro-3H-1,2,4-triazol-3-one, -4-methyl-5-methylthio-2,4-dihydro-3H-1,2,4-triazol-3-one, -4-methyl-5-ethylthio-2,4-dihydro-3H-1,2,4-triazol-3-one -4-methoxy-5-methyl-2,4-dihydro-3H-1,2,4-triazol-3-one, -4-methoxy-5-ethyl-2,4-dihydro-3H-1,2,4-triazol-3-one, -4-methoxy-5-n-propyl-2,4-dihydro-3H-1,2,4-triazol-3-one, -4-cyclopropyl-5-methoxy-2,4-dihydro-3H-1,2,4-triazol-3-one, -4-cyclopropyl-5-ethoxy-2,4-dihydro-3H-1,2, 4-triazol-3-one, -4-cyclopropyl-5-n-propoxy-2,4dihydro-3H-1,2,4-triazol-3-one, -4-cyclopropyl-5-i-propoxy-2,4-dihydro-3H-1,2,4-triazol-3-one and -4-cyclopropyl-5-trifluoroethoxy-2,4-dihydro-3H-1,2,4-triazol-3-one and the sodium and potassium salts of these compounds.

The compounds 2-(2-methoxycarbonyl-phenylsulphonylaminocarbonyl)-4-methyl-5-n-propoxy-2, 4-dihydro-3H-1,2,4-triazol-3-one (II-1) and 2-(2-trifluoromethoxy-phenylsulphonylaminocarbonyl)-4-methyl-5-methoxy-2,4-dihydro-3H-1,2,4-triazol-3-one (II-2) and their sodium salts—(II-1-Na salt and II-2-Na salt, respectively)—may be particularly emphasized as mixing components of the formula (II).

The compounds of the formula (II) are described in the patent applications or patents mentioned above for the N-arylsulphonylaminocarbonyl-triazolinones.

Surprisingly, it has now been found that the active compound combinations defined above of N-aryl-triazolinones of the general formula (I) and N-arylsulphonylaminocarbonyl-triazolinones of the general formula (II), in addition to being very well tolerated by useful plants, have particularly high herbicidal activity and can be used in a variety of crops, in particular in wheat, but additionally also in maize, barley and rice, for the selective control of weeds.

Surprisingly, the herbicidal activity of the active compound combinations according to the invention of compounds of the above mentioned groups 1 and 2 is considerably higher than the sum of the effects of the individual active compounds.

This means that there exists not only a complementary action but also an unforeseeable synergistic effect. The novel active compound combinations are tolerated well by a large number of crops, and the novel active compound combinations also effectively control weeds which are otherwise difficult to control. The novel active compound combinations are therefore a valuable addition to the selective herbicides.

The active compound combinations according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindemia, Lamium, Veronica, Abutilon, Emex, Datura Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compound combinations according to the invention is in no way restricted to these genera, but also extends in the same manner to other plants.

At specific concentration ratios, the synergistic effect of the active compound combinations according to the invention is particularly pronounced. However, the ratios by weight of the active compounds in the active compound combinations can be varied within relatively wide ranges. In general, 0.01 to 100 parts by weight, preferably 0.05 to 50 parts by weight and particularly preferably 0.1 to 10 parts by weight of active compound of group 2 are present per part by weight of active compound of the formula (I).

The active compound combinations can be converted into the customary formulations, such as solutions, emulsions, wettable powders, suspensions, powders, dusts, pastes, soluble powders, granules, suspo-emulsion concentrates, natural and synthetic substances impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

If the extender used is water it is also possible to use, for example, organic solvents as auxiliary solvents. Suitable liquid solvents are in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

Suitable solid carriers are:
for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifying and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; suitable dispersing agents are: for example lignin-sulphite waste liquors and methylcellulose.

Tackifiers such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95 per cent by weight, preferably between 0.5 and 90%, of active compounds.

In general, the active compound combinations according to the invention are applied in the form of ready mixes. However, the active compounds which the active compound combinations comprise can also be formulated individually and mixed upon use, i.e. applied in the form of tank mixes.

The novel active compound combinations can be used as such or in the form of their formulations, and furthermore also as mixtures with other known herbicides, ready mixes or tank mixes again being possible. They may also be mixed with other known active compounds, such as fungicides, insecticides, acaricides, nematicides, bird repellents, growth substances, plant nutrients and agents which improve soil structure. For particular application purposes, in particular when applied post-emergence, it may furthermore be advantageous to incorporate, in the formulations, mineral or vegetable oils which are tolerated by plants (for example the commercial product "Oleo DuPont 11E") or ammonium salts such as, for example, ammonium sulphate or ammonium thiocyanate, as further additives.

The novel active compound combinations can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, dusting or scattering.

The active compound combinations according to the invention can be applied before and after the plants have emerged, that is to say pre-emergence and post-emergence. They can also be incorporated into the soil before sowing.

The good herbicidal activity of the novel active compound combinations can be seen from the examples which follow. While the individual active compounds show weak points regarding the herbicidal activity, the combinations, without exception, display a very good activity against weeds, which exceeds a simple additive effect.

A synergistic effect in herbicides is always present when the herbicidal activity of the active compound combination exceeds the activity of the active compounds when applied individually.

The synergistic action of the novel active compound combinations is demonstrated by the examples below.

EXAMPLE A

Post-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants of a height of 5–15 cm are sprayed with the preparation of active compound such that the particular amounts of active compound desired are applied per unit area. The concentration of the spray liquor is chosen so that the particular amounts of active compound desired are applied at 1000 l of water/ha.

After three weeks, the degree of damage to the plants is rated in % damage in comparison to the development of the untreated control.

The figures denote:

0%=no effect (like untreated control)

100%=total destruction

TABLE A-1

Post-emergence test/greenhouse
For the test plants, the damage in percent is stated.

| Active compound or combination | Application rate (g of a.i./ha) | Wheat | Alopecurus | Abutilon | Datura | Ipomoea | Polygonum | Veronica |
|---|---|---|---|---|---|---|---|---|
| II-1 Na Salt | 30 | 20 | 70 | 80 | 70 | 70 | 60 | 50 |
| II-1 Na Salt + I-1 | 15 + 15 | 10 | 90 | 100 | 95 | 100 | 95 | 100 |

TABLE A-2

Post-emergence test/greenhouse
For the test plants, the damage in percent is stated.

| Active compound or combination | Application rate (g of a.i./ha) | Wheat | Alopecurus | Bromus | Echinochloa |
|---|---|---|---|---|---|
| I-1 | 30 | 15 | 20 | 20 | 30 |
| I-1 + II-1 Na Salt | 15 + 15 | 10 | 90 | 90 | 95 |

TABLE A-3

Post-emergence test/greenhouse
For the test plants, the damage in percent is stated.

| Active compound or combination | Application rate (g of a.i./ha) | Wheat | Lolium | Abutilon | Ipomoea | Matricaria |
|---|---|---|---|---|---|---|
| II-2 Na Salt | 30 | 30 | 70 | 60 | 70 | 80 |
| II-2 Na Salt + I-1 | 15 + 15 | 5 | 90 | 100 | 100 | 100 |

TABLE A-4

Post-emergence test/greenhouse
For the test plants, the damage in percent is stated.

| Active compound or combination | Application rate (g of a.i./ha) | Wheat | Alopecurus | Avena fatua | Bromus | Echinochloa | Lolium | Setaria | Sorghum | Viola |
|---|---|---|---|---|---|---|---|---|---|---|
| I-1 | 30 | 15 | 20 | 20 | 20 | 30 | 30 | 40 | 50 | 40 |
| I-1 + II-2 Na Salt | 15 + 15 | 5 | 70 | 70 | 90 | 80 | 90 | 90 | 95 | 80 |

TABLE A-5

Post-emergence test/greenhouse
For the test plants, the damage in percent is stated.

| Active compound or combination | Application rate (g of a.i./ha) | Wheat | Abutilon | Chenopodium | Datura | Galium | Matricaria | Polygonum | Veronica |
|---|---|---|---|---|---|---|---|---|---|
| II-1 Na Salt | 30 | 10 | 50 | 70 | 60 | 60 | 70 | 40 | 50 |
| II-1 Na Salt + I-2 | 15 + 15 | 5 | 100 | 100 | 90 | 100 | 90 | 95 | 100 |

TABLE A-6

Post-emergence test/greenhouse
For the test plants, the damage in percent is stated.

| Active compound or combination | Application rate (g of a.i./ha) | Wheat | Alopecurus | Bromus | Echinochloa | Polygonum | Viola |
|---|---|---|---|---|---|---|---|
| I-2 | 30 | 10 | 20 | 40 | 40 | 70 | 60 |
| I-2 + II-1 Na Salt | 15 + 15 | 5 | 80 | 80 | 90 | 95 | 90 |

TABLE A-7

Post-emergence test/greenhouse
For the test plants, the damage in percent is stated.

| Active compound or combination | Application rate (g of a.i./ha) | Wheat | Abutilon | Cassia | Chenopodium | Datura | Ipomoea | Polygonum | Veronica | Viola |
|---|---|---|---|---|---|---|---|---|---|---|
| II-1 Na Salt | 30 | 10 | 50 | 60 | 70 | 60 | 80 | 40 | 50 | 70 |
| II-1 Na Salt + I-3 | 15 + 15 | 0 | 95 | 80 | 100 | 95 | 100 | 95 | 95 | 95 |

TABLE A-8

Post-emergence test/greenhouse
For the test plants, the damage in percent is stated

| Active compound or combination | Application rate (g of a.i./ha) | Wheat | Alopecurus | Bromus | Cyperus | Echinochloa |
|---|---|---|---|---|---|---|
| I-3 | 30 | 0 | 10 | 30 | 50 | 50 |
| I-3 + II-1 Na Salt | 15 + 15 | 0 | 70 | 80 | 80 | 90 |

TABLE A-9

Post-emergence test/greenhouse
For the test plants, the damage in percent is stated.

| Active compound or combination | Application rate (g of a.i./ha) | Wheat | Bromus | Abutilon | Chenopodium | Datura | Galium | Matricaria | Polygonum | Veronica |
|---|---|---|---|---|---|---|---|---|---|---|
| II-1 Na Salt | 30 | 10 | 70 | 50 | 70 | 60 | 60 | 70 | 40 | 50 |
| II-1 Na Salt + I-4 | 15 + 15 | 10 | 90 | 100 | 100 | 95 | 95 | 95 | 100 | 100 |

TABLE A-10

Post-emergence test/greenhouse
For the test plants, the damage in percent is stated

| Active compound or combination | Application rate (g of a.i./ha) | Wheat | Alopecurus | Bromus | Echinochloa |
|---|---|---|---|---|---|
| I-4 | 30 | 15 | 20 | 30 | 60 |
| I-4 + II-1 Na Salt | 15 + 15 | 10 | 80 | 90 | 90 |

TABLE A-14

Post-emergence test/greenhouse
For the test plants, the damage in percent is stated.

| Active compound or combination | Application rate (g of a.i./ha) | Wheat | Alopecurus | Avena fatua | Bromus | Echinochloa |
|---|---|---|---|---|---|---|
| I-3 | 30 | 0 | 10 | 20 | 30 | 50 |
| I-3 + II-2 Na Salt | 15 + 15 | 10 | 50 | 60 | 70 | 80 |

TABLE A-11

Post-emergence test/greenhouse
For the test plants, the damage in percent is stated.

| Active compound or combination | Application rate (g of a.i./ha) | Wheat | Abutilon | Chenopodium | Galium | Ipomoea | Xantium |
|---|---|---|---|---|---|---|---|
| II-2 Na Salt | 30 | 15 | 60 | 70 | 50 | 80 | 80 |
| II-2 Na Salt + I-2 | 15 + 15 | 10 | 100 | 95 | 95 | 100 | 95 |

TABLE A-12

Post-emergence test/greenhouse
For the test plants, the damage in percent is stated.

| Active compound or combination | Application rate (g of a.i./ha) | Wheat | Avena fatua | Bromus | Echinochloa | Setaria | Polygonum |
|---|---|---|---|---|---|---|---|
| I-2 | 30 | 10 | 20 | 40 | 40 | 50 | 70 |
| I-2 + II-2 Na Salt | 15 + 15 | 10 | 70 | 70 | 90 | 90 | 95 |

TABLE A-13

Post-emergence test/greenhouse
For the test plants, the damage in percent is stated.

| Active compound or combination | Application rate (g of a.i./ha) | Wheat | Abutilon | Chenopodium | Ipomoea | Veronica | Viola |
|---|---|---|---|---|---|---|---|
| II-2 Na Salt | 30 | 15 | 60 | 70 | 80 | 60 | 80 |
| II-2 Na Salt + I-3 | 15 + 15 | 10 | 90 | 100 | 100 | 95 | 100 |

TABLE A-15

Post-emergence test/greenhouse
For the test plants, the damage in percent is stated.

| Active compound or combination | Application rate (g of a.i./ha) | Wheat | Abutilon | Chenopodium | Ipomoea | Matricaria | Veronica | Viola |
|---|---|---|---|---|---|---|---|---|
| II-2 Na Salt | 30 | 15 | 60 | 70 | 80 | 70 | 60 | 80 |
| II-2 Na Salt + I-4 | 15 + 15 | 10 | 95 | 100 | 100 | 100 | 95 | 95 |

TABLE A-16

Post-emergence test/greenhouse
For the test plants, the damage in percent is stated.

| Active compound or combination | Application rate (g of a.i./ha) | Wheat | Echinochloa | Setaria |
|---|---|---|---|---|
| I-4 | 30 | 15 | 60 | 40 |
| I-4 + II-2 Na Salt | 15 + 15 | 10 | 80 | 70 |

What is claimed is:

1. A herbicidal composition, which comprises an active compound combination comprising
   (a) at least one N-aryl-triazolin(ethi)one of the general formula (I)

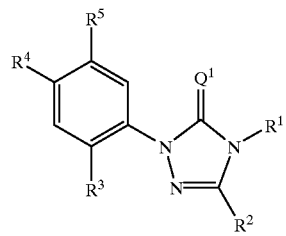

wherein
$Q^1$ represents oxygen or sulphur,
$R^1$ represents unsubstituted or halogen-substituted alkyl having 1 to 5 carbon atoms,
$R^2$ represents unsubstituted or halogen-substituted alkyl having 1 to 5 carbon atoms,
$R^3$ represents hydrogen or halogen,
$R^4$ represents cyano, thiocarbamoyl or halogen, and
$R^5$ represents nitro, cyano, carboxyl, carbamoyl, thiocarbamoyl, hydroxyl, mercapto, amino, hydroxyamino, aminosulphonyl, halogen, represents in each case unsubstituted or cyano-, hydroxyl-, $C_1$–$C_4$-alkoxy-, $C_1$–$C_4$-alkyl-carbonyl- or $C_1$–$C_4$-alkoxy-carbonyl-substituted alkyl, alkoxy, alkylthio, alkylsulphinyl, alkylsulphonyl, alkylcarbonyl, alkoxycarbonyl or alkylamino having in each case 1 to 6 carbon atoms, represents in each case unsubstituted or cyano-, carboxyl-, halogen- or $C_1$–$C_4$-alkoxy-carbonyl-substituted alkenyl, alkynyl, alkenyloxy or alkynyloxy having in each case 2 to 6 carbon atoms, represents in each case unsubstituted or halogen-substituted alkylcarbonylamino, alkoxy-carbonylamino, alkylsulphonylamino, N,N-bis-alkylsulphonyl-amino or N-alkylcarbonyl-N-alkylsulphonyl-amino having in each case 1 to 6 carbon atoms in the alkyl group, or represents in each case unsubstituted or cyano-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted N-phenylcarbonyl-N-alkylsulphonyl-amino, N-pyridylcarbonyl-N-alkylsulphonyl-amino, N-furylcarbonyl-N-alkylsulphonyl-amino or N-thienylcarbonyl-N-alkylsulphonyl-amino having in each case 1 to 6 carbon atoms in the alkyl group, and
   (b) at least one N-arylsulphonylamino(thio)carbonyl-triazolin(ethi)one of the general formula (II)

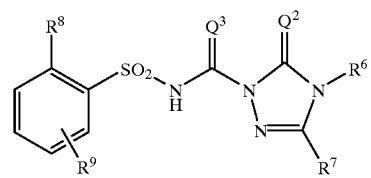

wherein
$Q^2$ and $Q^3$ each represent oxygen or sulphur,
$R^6$ represents in each case unsubstituted or cyano-, halogen- or $C_1$–$C_4$-alkoxy-substituted alkyl, alkenyl, alkynyl, alkoxy, alkenyloxy, alkylamino or dialkylamino having in each case up to 6 carbon atoms, or represents in each case unsubstituted or cyano-, halogen- or $C_1$–$C_4$-alkyl-substituted cycloalkyl, cycloalkylalkyl or cycloalkylamino having in each case 3 to 6 carbon atoms in the cycloalkyl group is and 0 to 4 carbon atoms in the alkyl moiety,
$R^7$ represents hydrogen, represents halogen, represents in each case unsubstituted or cyano-, halogen- or $C_1$–$C_4$-alkoxy-substituted alkyl, alkoxy, alkylthio, alkylamino, dialkylamino, alkenyl, alkynyl, alkenyloxy, alkynyloxy, alkenylthio, alkynylthio, alkenylamino or alkynylamino having in each case up to 6 carbon atoms, or represents in each case unsubstituted or cyano-, halogen- or $C_1$–$C_4$-alkyl-substituted cycloalkyl, cycloalkyloxy, cycloalkylthio, cycloalkylamino or cycloalkylalkyl having in each case 3 to 6 carbon atoms in the cycloalkyl group and 0 to 4 carbon atoms in the alkyl moiety,
$R^8$ represents nitro, cyano, halogen, phenyl, phenoxy, represents in each case unsubstituted or cyano-, halogen- or $C_1$–$C_4$-alkoxy-substituted alkyl, alkylcarbonyl, alkoxy, alkoxycarbonyl, alkylthio, alkylsulphinyl, alkylsulphonyl, dialkylaminosulphonyl, alkylamino, alkenyl, alkenyloxy, alkenylthio, alkenylamino, alkynyl, alkynyloxy, alkynylthio having in each case up to 6 carbon atoms, or represents in each case unsubstituted or cyano-, halogen- or $C_1$–$C_4$-alkyl-substituted cycloalkyl, cycloalkyloxy, cycloalkylthio, cycloalkylamino having in each case 3 to 6 carbon atoms in the cycloalkyl group, and $R^9$ represents hydrogen, nitro, cyano, halogen, phenyl, phenoxy, represents in each case unsubstituted or cyano-, halogen- or $C_1$–$C_4$-alkoxy-substituted alkyl, alkylcarbonyl, alkoxy, alkoxycarbonyl, alkylthio, alkylsulphinyl, alkylsulphonyl, alkylamino, alkenyl, alkenyloxy, alkenylthio, alkenylamino, alkynyl, alkynyloxy or alkynylthio having in each case up to 6 carbon atoms, or represents in each case unsubstituted or cyano-, halogen- or $C_1$–$C_4$-alkyl-substituted cycloalkyl, cycloalkyloxy, cycloalkylthio, cycloalkylamino having in each case 3 to 6 carbon atoms in the cycloalkyl group, or a salt of a compound of the formula (II).

2. A herbicidal composition according to claim 1, wherein $R^2$ represents an unsubstituted or halogen-substituted methyl, ethyl, n- or i-propyl, n-, i-, s- or t-butyl.

3. A herbicidal composition according to claim 1, wherein one or both of $Q^2$ and $Q^3$ represents sulphur.

4. A herbicidal composition according to claim 1, wherein the N-aryl-triazolin(ethi)one of general formula (I) is selected from the compounds 2-(4-thiocarbamoyl-2-fluoro-5-ethylsulphonylamino-phenyl)-4-methyl-5-trifluoromethyl-2,4-dihydro-3H-1,2,4-triazol-3-one and 2-(4-cyano-2-fluoro-5-ethylsulphonylaminophenyl)-4-methyl-5-trifluoromethyl-2,4-dihydro-3H-1,2,4-triazol-3-one, and the N-arylsulphonylamino-(thio)carbonyl-triazolin (ethi)one of general formula (II) is selected from the compounds 2-(2-methoxycarbonyl-phenylsulphonylaminocarbonyl) 4-methyl-5-n-propoxy-2,4-dihydro-3H-1,2,4-triazol-3-one, 2-(2-trifluoromethoxy-phenylsulphonylaminocarbonyl)4-methyl-5-methoxy-2,4-dihydro-3H-1,2,4-triazol-3-one and their sodium salts.

5. A herbicidal composition according to claim 1, having a N-aryl-sulphonylamino(thio)carbonyl-triazolin(ethi)one to N-aryl-triazolin(ethi)one weight ratio of 0.01:1 to 100:1.

6. A herbicidal composition according to claim 1, having a N-aryl-sulphonylamino(thio)carbonyl-triazolin(ethi)one to N-aryl-triazolin(ethi)one weight ratio of 0.05:50 to 100:1.

7. A herbicidal composition according to claim 1, having a N-aryl-sulphonylamino(thio)carbonyl-triazolin(ethi)one to N-aryl-triazolin(ethi)one weight ratio of 0.1:1 to 10:1.

8. The herbicidal composition of claim 1, comprising an active compound combination comprising (a) at least one N-aryl-triazolin(ethi)one of the general formula (I)

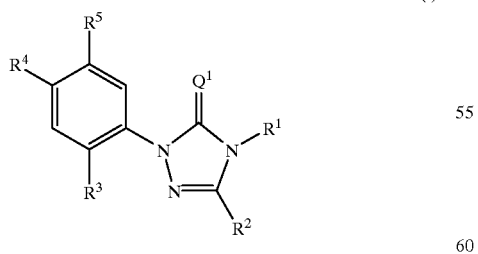

(I)

wherein $Q^1$ represents oxygen or sulphur, $R^1$ represents in each case unsubstituted or halogen-substituted methyl, ethyl, n- or i-propyl, n-, i-, s- or t-butyl wherein the substituent is selected from the group consisting of fluorine and chlorine, $R^2$ represents in each case unsubstituted or halogen-substituted methyl, ethyl, n- or i-propyl, n-, i-, s- or t-butyl wherein the substitutent is selected from the group consisting of fluorine and chlorine, $R^3$ represents hydrogen, fluorine, chlorine or bromine, $R^4$ represents cyano, thiocarbamoyl, fluorine, chlorine or bromine, and $R^5$ represents nitro, cyano, carboxyl, carbamoyl, thiocarbamoyl, hydroxyl, mercapto, amino, hydroxyamino, aminosulphonyl, fluorine, chlorine, bromine, represents in each case unsubstituted or cyano-, hydroxyl-, methoxy-, ethoxy-, acetyl-, propionyl-, methoxycarbonyl- or ethoxy-carbonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, methylsulphonyl, ethylsulphonyl, acetyl, propionyl, n- or i-butyroyl, methoxycarbonyl, ethoxycarbonyl, n- or i-propoxycarbonyl, methylamino, ethylamino, n- or i-propylamino, n-, i-, s- or t-butylamino, represents in each case unsubstituted or cyano-, carboxyl-, fluorine-, chlorine-, bromine-, methoxycarbonyl- or ethoxycarbonyl-substituted ethenyl, propenyl, butenyl, ethenyl, propinyl, butinyl, propenyloxy, butenyloxy, propinyloxy or butinyloxy, represents in each case unsubstituted or halogen-substituted acetylamino, propionylamino, methoxycarbonylamino, ethoxycarbonylamino, methylsulphonyl-amino, ethylsulphonylamino, n- or i-propylsulphonylamino, n-, i-, s- or t-butylsulphonylamino, N,N-bis-methylsulphonyl-amino, N,N-bis-ethylsulphonyl-amino, N-ethylsulphonyl-N-methylsulphonyl-amino, N-acetyl-N-methylsulphonyl-amino, N-propionyl-N-methylsulphonyl-amino, N-n-butyroyl-N-methylsulphonyl-amino, N-i-butyroyl-N-methylsulphonyl-amino, N-acetyl-N-ethylsulphonyl-amino, N-propionyl-N-ethylsulphonyl-amino, N-n-butyroyl-N-ethylsulphonyl-amino, N-i-butyroyl-N-ethylsulphonyl-amino wherein the substituent is selected from the group consisting of fluorine and chlorine, or represents in each case unsubstituted or cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted N-phenylcarbonyl-N-methylsulphonyl-amino, N-phenylcarbonyl-N-ethylsulphonyl-amino, N-thienylcarbonyl-N-methylsulphonyl-amino or N-thienylcarbonyl-N-ethylsulphonyl-amino, and (b) at least one N-arylsulphonylamino(thio)carbonyl-riazolin(ethi)one of the general formula (II)

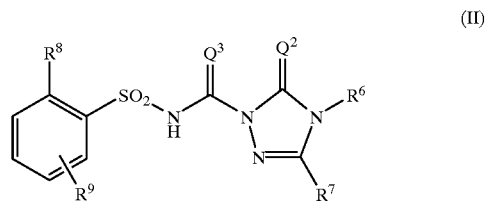

(II)

wherein $Q^2$ and $Q^3$ each represent oxygen or sulphur, $R^6$ represents in each case unsubstituted or cyano-, fluorine-, chlorine-, methoxy- or ethoxy-substituted methyl, ethyl, n- or i-propyl, n-, i-, s- or t-butyl, ethenyl, propenyl, butenyl, ethenyl, propinyl, butinyl, methoxy, ethoxy, n- or i-propoxy, n-, i-, s- or t-butoxy, propenyloxy, butenyloxy, methylamino, ethylamino, n- or i-propylamino, n-, i-, s- or t-butylamino, dimethylamino or diethylamino, or represents in each case unsubstituted or cyano-, fluorine-, chlorine-, bromine-, methyl-, ethyl-, n- or i-propyl-substituted cyclopropyl, cyclobutyl, cyclopentyl, cyclohexyl, cyclopropylmethyl, cyclobutylmethyl, cyclopentylmethyl, cyclohexylmethyl, cyclopropylamino, cyclobutylamino, cyclopentylamino or cyclohexylamino, $R^7$ represents fluorine, chlorine, bromine, represents in each case unsubstituted or cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino, diethylamino, ethenyl, propenyl, butenyl, ethenyl, propinyl, butinyl, ethenyloxy, propenyloxy, butenyloxy, propinyloxy, butinyloxy, ethenylthio, propenylthio, butenylthio, propinylthio, butinylthio, propenylamino, butenylamino, propinylamino or butinylamino, or represents in each case unsubstituted or cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl or cyclohexylmethyl, $R^8$ represents nitro, cyano, fluorine, chlorine, bromine, represents in each case unsubstituted or cyano-, fluorine-, chlorine-, methoxy- or ethoxy-substituted methyl, ethyl, n- or i-propyl, n-, i-, s- or t-butyl, acetyl, propionyl, n- or i-butyroyl, methoxy, ethoxy, n- or i-propoxy, n-, i-, s- or t-butoxy, methoxycarbonyl, ethoxycarbonyl, n- or i-propoxycarbonyl, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, ethenyl, propenyl, butenyl, propenyloxy, butenyloxy, propenylthio, butenylthio, propenylamino, butenylamino, ethenyl, propinyl, butinyl, propinyloxy, butinyloxy, propinylthio or butinylthio, or represents in each case unsubstituted or cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino, $R^9$ represents hydrogen, nitro, cyano, fluorine, chlorine, bromine, represents in each case unsubstituted or cyano-, fluorine-, chlorine-, methoxy- or ethoxy-substituted methyl, ethyl, n- or i-propyl, n-, i-, s- or t-butyl, acetyl, propionyl, n- or i-butyroyl, methoxy, ethoxy, n- or i-propoxy, n-, i-, s- or t-butoxy, methoxycarbonyl, ethoxycarbonyl, n- or i-propoxycarbonyl, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, ethenyl, propenyl, butenyl, propenyloxy, butenyloxy, propenylthio, butenylthio, propenylamino, butenylamino, ethenyl, propinyl, butinyl, propinyloxy, butinyloxy, propinylthio or butinylthio, or represents in each case unsubstituted or cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino, or a salt of a compound of the formula (II).

9. A herbicidal composition according to claim 8, having a N-aryl-sulphonylamino(thio)carbonyl-triazolin(ethi)one to N-aryl-triazolin(ethi)one weight ratio of 0.01:1 to 100:1.

10. A herbicidal composition according to claim 8, having a N-aryl-sulphonylamino(thio)carbonyl-triazolin(ethi)one to N-aryl-triazolin(ethi)one weight ratio of 0.05:50 to 100:1.

11. A herbicidal composition according to claim 8, having a N-aryl-sulphonylamino(thio)carbonyl-triazolin(ethi)one to N-aryl-triazolin(ethi)one weight ratio of 0.1:1 to 10:1.

12. The herbicidal composition of claim 1 comprising an active compound combination comprising
(a) at least one N-aryl-triazolin(ethi)one of the general formula (I)

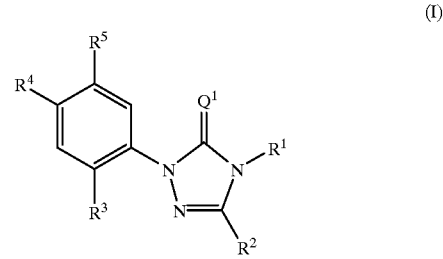

wherein

Q1 represents oxygen or sulphur, $R^1$ represents methyl, ethyl or difluoromethyl, $R^2$ represents methyl, ethyl, difluoromethyl, trifluoromethyl, fluoroethyl, difluoroethyl, trifluoroethyl, tetrafluoroethyl or pentafluoroethyl, $R^3$ represents fluorine or chlorine, $R^4$ represents cyano, thiocarbamoyl, chlorine or bromine, and $R^5$ represents nitro, cyano, carboxyl, carbamoyl, thiocarbamoyl, hydroxyl, mercapto, amino, fluorine, chlorine, bromine, represents in each case unsubstituted or cyano-, methoxy-, ethoxy-, methoxycarbonyl- or ethoxycarbonyl-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, methoxycarbonyl, ethoxycarbonyl, n- or i-propoxycarbonyl, methylamino, ethylamino, n- or i-propylamino, represents in each case unsubstituted or cyano-, carboxyl-, fluorine-, chlorine-, bromine-, methoxycarbonyl- or ethoxycarbonyl-substituted ethenyl or propenyl, represents propenyloxy, butenyloxy, propinyloxy or butinyloxy, represents in each case unsubstituted or halogen-substituted methylsulphonyl-amino, ethylsulphonylamino, n- or i-propylsulphonylamino, n-, i-, s- or t-butylsulphonylamino, N,N-bis-methylsulphonyl-amino, N,N-bis-ethylsulphonyl-amino, N-ethylsulphonyl-N-methylsulphonyl-amino, N-acetyl-N-methylsulphonyl-amino, N-propionyl-N-methylsulphonyl-amino, N-n-butyroyl-N-methylsulphonyl-amino, N-i-butyroyl-N-methylsulphonyl-amino, N-acetyl-N-ethylsulphonyl-amino, N-propionyl-N-ethylsulphonyl-amino, N-n-butyroyl-N-ethylsulphonyl-amino, N-i-butyroyl-N-ethylsulphonyl-amino wherein the substituent is selected from the group consisting of fluorine and chlorine, or represents in each case unsubstituted or cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted N-phenylcarbonyl-N-methylsulphonyl-amino, N-phenylcarbonyl-N-ethylsulphonyl-amino, N-thienylcarbonyl-N-methylsulphonyl-amino or N-thienylcarbonyl-N-ethylsulphonyl-amino, and (b) at least one N-arylsulphonylamino(thio)carbonyl-triazolin(ethi)one of the general formula (II)

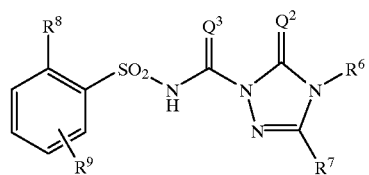

(II)

wherein $Q^2$ and $Q^3$ each represent oxygen or sulphur, $R^6$ represents in each case unsubstituted or fluorine-, chlorine-, methoxy- or ethoxy-substituted methyl, ethyl, methoxy or ethoxy, or represents cyclopropyl, $R^7$ represents chlorine, bromine, represents in each case unsubstituted or fluorine-, chlorine-, methoxy- or ethoxy-substituted methyl, ethyl, n- or i-propyl, methoxy, ethoxy, n- or i-propoxy, methylthio, ethylthio, n- or i-propylthio, methylamino, ethylamino, n- or i-propylamino, represents dimethylamino, propenylthio, propinylthio or represents cyclopropyl, $R^8$ represents fluorine, chlorine, bromine, represents in each case unsubstituted or fluorine-, chlorine-, methoxy- or ethoxy substituted methyl, ethyl, n- or i-propyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, or represents cyclopropyl, $R^9$ represents hydrogen, nitro, cyano, fluorine, chlorine, bromine, represents in each case unsubstituted or fluorine-, chlorine-, methoxy- or ethoxy-substituted methyl, ethyl, n- or i-propyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, n- or i-propylsulphinyl, methylsulphonyl, ethylsulphonyl, n- or i-propylsulphonyl, or represents cyclopropyl, or a salt of a compound of the formula (II).

13. A herbicidal composition according to claim 12, having a N-aryl-sulphonylamino(thio)carbonyl-triazolin(ethi)one to N-aryl-triazolin(ethi)one weight ratio of 0.01:1 to 100:1.

14. A herbicidal composition according to claim 12, having a N-aryl-sulphonylamino(thio)carbonyl-triazolin(ethi)one to N-aryl-triazolin(ethi)one weight ratio of 0.05:50 to 100:1.

15. A herbicidal composition according to claim 12, having a N-aryl-sulphonylamino(thio)carbonyl-triazolin(ethi)one to N-aryl-triazolin(ethi)one weight ratio of 0.1:1 to 10:1.

16. A process for preparing a herbicidal composition comprising the step of mixing at least one N-aryltriazolin(ethi)one of claim 1 with at least one N-arylsulphonylamino(thio)carbonyl-triazolin(ethi)one of claim 1 and at least one extender, or surface-active agent.

17. A method for controlling undesirable plants, comprising the step of applying the herbicidal composition of claim 1 to the plants or their habitat.

* * * * *